(12) United States Patent
Kalergis Parra et al.

(10) Patent No.: US 12,098,185 B2
(45) Date of Patent: Sep. 24, 2024

(54) MONOCLONAL ANTIBODY 11B2C7 OR FRAGMENT THEREOF, THAT SPECIFICALLY RECOGNIZES HERPES SIMPLEX VIRUS 1 AND 2

(71) Applicants: PONTIFICIA UNIVERSIDAD CATOLICA DE CHILE, Santiago (CL); FUNDACION COPEC UNIVERSIDAD CATÓLICA, Santiago (CL)

(72) Inventors: Alexis Kalergis Parra, Santiago (CL); Susan Bueno Ramírez, Santiago (CL); Pablo Gonzalez Muñoz, Santiago (CL)

(73) Assignees: PONTIFICIA UNIVERSIDAD CATOLICA DE CHILE, Santiago (CL); FUNDACION COPEC UNIVERSIDAD CATÓLICA, Santiago (CL)

( * ) Notice: Subject to any disclaimer, the term of this patent is extended or adjusted under 35 U.S.C. 154(b) by 850 days.

(21) Appl. No.: 17/272,050

(22) PCT Filed: Aug. 28, 2018

(86) PCT No.: PCT/CL2018/050075
§ 371 (c)(1),
(2) Date: Feb. 26, 2021

(87) PCT Pub. No.: WO2020/041911
PCT Pub. Date: Mar. 5, 2020

(65) Prior Publication Data
US 2021/0347857 A1    Nov. 11, 2021

(51) Int. Cl.
*C07K 16/08*    (2006.01)
*G01N 33/569*   (2006.01)

(52) U.S. Cl.
CPC ..... *C07K 16/087* (2013.01); *G01N 33/56994* (2013.01); *C07K 2317/24* (2013.01); *C07K 2317/565* (2013.01); *G01N 2333/035* (2013.01)

(58) Field of Classification Search
None
See application file for complete search history.

(56) References Cited

U.S. PATENT DOCUMENTS

| 6,156,313 | A  | 12/2000 | Burton et al. |
| 2005/0130132 | A1 | 6/2005 | Day et al. |
| 2012/0282260 | A1 | 11/2012 | Lai et al. |
| 2016/0158344 | A1 | 6/2016 | Davies et al. |

FOREIGN PATENT DOCUMENTS

| CA | 2 950 489 | 12/2015 | |
| CN | 105925537 | 9/2016 | |
| EP | 3 050 897 | 8/2016 | |
| WO | 2015/095366 | 6/2015 | |
| WO | WO-2020041910 A1 * | 3/2020 | ........... C07K 16/085 |

OTHER PUBLICATIONS

International Search Report issued in International Application No. PCT/CL2018/050075, Feb. 12, 2019, 8 pages with translation.
Kalantari-Dehaghi, et al., "Discovery of Potential Diagnostic and Vaccine Antigens in Herpes Simplex Virus 1 and 2 by Proteome-Wide Anitbody Profiling", Journal of Virology, vol. 86, No. 8, Apr. 2012, pp. 4328-4339.
Sheaffer, et al., "Evidence for controlled incorporation of herpes simplex virus type 1 UL26 protease into capsids", Journal of Virology, vol. 74, No. 15, Aug. 2000, pp. 6838-6848.

* cited by examiner

*Primary Examiner* — Meera Natarajan
*Assistant Examiner* — Cheom-Gil Cheong
(74) *Attorney, Agent, or Firm* — HSML P.C.

(57) ABSTRACT

The present invention refers to a new monoclonal antibody or fragment thereof, called 11B2C7, which specifically recognizes herpes simplex virus (HSV), in its two types, herpes simplex virus type 1 and herpes simplex virus type 2 (HSV-1 and HSV-2). Preferably, the antibody of the invention is useful for the development of methods for the diagnosis of herpes simplex virus infection, as well as for the production of pharmaceutical compositions intended for the treatment, protection and/or prophylaxis of infection specifically caused by HSV-1 and HSV-2.

12 Claims, 5 Drawing Sheets
Specification includes a Sequence Listing.

MONOCLONAL ANTIBODY 11B2C7 OR FRAGMENT THEREOF, THAT SPECIFICALLY RECOGNIZES HERPES SIMPLEX VIRUS 1 AND 2

FIELD OF INVENTION

The present invention relates to a novel monoclonal antibody or fragment thereof, which specifically recognizes herpes simplex virus (HSV), in its two types, herpes simplex virus type 1 and herpes simplex virus type 2 (HSV-1 and HSV-2).

Preferably, the antibody of the invention is useful for the development of methods for the diagnosis of herpes simplex virus infection, as well as for the production of pharmaceutical compositions intended for the treatment, protection and/or prophylaxis of infection specifically caused by HSV-1 and HSV-2.

BACKGROUND OF THE INVENTION

Viruses of the group of alphaherpesviruses, such as herpes simplex virus type 1 (HSV-1), herpes simplex virus type 2 (HSV-2) and varicella zoster virus (VZV) affect the general population with high prevalence, manifesting itself with a wide spectrum of pathologies that range from prolonged and painful skin lesions, eye infection, mucosal lesions, pneumonia and even encephalitis. As indicated, the invention focuses on 2 of these viruses, HSV-1 and HSV-2.

HSV-1 is currently the leading cause of infection blindness in developed countries. HSV-1 is also the leading cause of primary genital herpes (cousin infection) and the leading cause of viral encephalitis in adults. The prevalence of this virus is estimated at around 70% in the world and is high in both developed and developing countries. In the US, the current prevalence of HSV-1 is 54%.

On the other hand, HSV-2 is the main cause of recurrent genital lesions and the main cause of neonatal encephalitis, which can be fatal and produces important sequelae in neonates. A worldwide prevalence of between 10-20% is estimated for HSV-2.

A persistent problem in the current diagnosis of infections by these alphaherpes viruses is that many of the clinical manifestations produced by HSV-1 and HSV-2 can be confused with lesions and pathologies produced by other viral and bacterial pathogens.

Currently the diagnosis of infection by HSV-1 and HSV-2 is made mainly by serology or qPCR. The first method usually does not report the timing or location of the infection and may be of limited utility in individuals previously infected with the virus. On the other hand, the second method is expensive and requires highly qualified personnel, as well as high-value laboratory supplies and equipment. Furthermore, qPCR could be too sensitive a technique considering the prevalence of the virus in the population, leading to obtaining false positives in the diagnosis. With this, diagnostic methods for HSV-1, HSV-2 and VZV that are fast, easy to use and at a low selling price would allow for having an instant diagnosis at the consultation site, allowing immediate treatment, ruling out infection by other pathogens and indicate prognosis. Having a rapid test eliminates the need for patients to reschedule a medical consultation, since the diagnosis is in situ.

On the other hand, an immediate diagnosis can be very useful for physicians treating immunosuppressed or immunodeficient patients, since these individuals are highly susceptible to herpes virus infections and tend to manifest severe and widespread pathologies with these viruses, compared to healthy patients. In all cases, a positive diagnosis for HSV-1 or HSV-2 would allow the doctor to indicate immediate treatment with existing antivirals, thus reducing the duration and severity of the disease. Furthermore, the determination of infection by HSV-1, HSV-2 allows the doctor to inform the patient of his prognosis, depending on the viral type involved and the place of infection.

The invention comprises a new monoclonal antibody capable of detecting the capsid antigens of HSV-1 and HSV-2 viruses: The detection of these viruses can be carried out in a preferred modality, using the sandwich ELISA technique, which can be easily and appropriately implemented in a rapid immunochromatographic type detection kit, easy to perform and interpret, with low production costs and therefore a low selling price, to detect the presence of herpes simplex virus type 1 and type 2, in samples obtained from swabs of skin lesions, eye swabs, mucous swabs, or in samples of plasma or encephalo-spinal fluid, among others.

The reduction in costs and delivery time of the result, added to a high specificity of the detection, given by the antibody of the invention, allow a greater public accessibility for the diagnosis of infections caused by the alphaherpes viruses HSV-1 and HSV-2 and an alternative of rapid detection to decide and start as soon as possible, the corresponding treatment, according to the results delivered by the analysis of biological samples, with the antibody that is part of the invention that we disclose here.

In this way, the invention translates into an antibody capable of detecting low amounts of HSV-1 and HSV-2 antigens, specifically, which allows the development of an alternative method of rapid, efficient and accurate detection and diagnosis for patients infected with any of these viruses, in order to determine an early and adequate treatment that allows a timely treatment of the disease. Furthermore, the efficiency of our antibody makes it possible to propose its use for the preparation of pharmaceutical compositions intended for the treatment and/or prophylaxis of infection by human pathogenic viruses such as type 1 and type 2 herpes simplex viruses.

The antibody of the invention corresponds specifically to a monoclonal antibody that specifically recognizes the VP21 protein of the capsid of the herpes simplex virus type 1 (HSV-1), but is capable of recognizing both the presence of HSV-1 and of HSV-2 in samples infected with these viruses.

As described in detail below, this invention is based on the inventors' choice to obtain antibodies capable of being used to detect the presence of the human pathogenic viruses, HSV-1 and HSV-2. As part of the research carried out and the strategy to obtain appropriate antibodies, it was decided to modify the codon use of *E. coli*, the nucleotide sequence of the UL26 gene of the herpes simplex virus HSV-1, which was overexpressed in *E. coli*, and subsequently isolated the amino acid product of said gene, the VP21 capsid protein of HSV-1. The isolated recombinant protein was used to immunize mice and subsequently obtain, by standard techniques, the monoclonal hybridoma of the invention that was named 11B2C7, and that secretes the antibody of the invention 11B2C7, whose characterization is given below.

In the state of the art prior to this invention there are some publications that are close to the invention, which are briefly summarized below.

In patent application CN105925537, a hybridoma cell and a monoclonal antibody are disclosed for the detection of HSV. This document discloses the CDR1 and 2 sequences of both the heavy chain and the light chain of the antibody that they disclose; sequences that differ from the CDRs of the antibody of the invention, therefore this document does not advance the antibody of the invention.

European patent EP3050897 discloses a monoclonal antibody for passive immunotherapy of infections caused by HSV-1 and HSV-2 herpes simplex. The EP3050897 antibody is characterized by four coding sequences for CDRs and corresponding coding sequences for the heavy and light chains respectively. Although this document aims at antibodies capable of binding to HSV-1 and HSV-2, its objective is not to detect the presence of these viruses and more importantly, the sequences claimed in EP3050897 differ from the antibody of the invention that here it is protected.

In the North American patent application US2005130132, the detection of herpes simplex virus is protected, for which monoclonal antibodies that detect HSV-2 viruses are obtained, but it is not mentioned that the antibodies produced were obtained using VP21 of HSV-1 as antigen for immunization. Furthermore, the amino acid sequences claimed in said document do not correspond to those of the antibody of the invention disclosed herein.

WO2015095366, this document seeks to protect a method of detecting antibodies against HSV-1 and HSV-2 in the serum of a patient, reacting the serum of the patient against antigens of these viruses immobilized in a matrix. The foregoing indicates that WO2015095366 seeks to detect the presence of antibodies and does not include the direct detection of viruses, so it calls for an invention other than the one protected here.

Thus, it is evident that the current state of the art for the detection of HSV-1 and HSV-2 requires the development of new procedures that facilitate and accelerate the obtaining of the result, both in reducing the time needed and not the need for qualified personnel to carry out the determination of the presence or absence of infection by HSV-1 and/or HSV2.

The invention solves this need by providing to the state of the art, a monoclonal antibody capable of detecting, with high specificity, the presence of the infectious viruses HSV-1 and HSV-2.

This antibody is useful for use in rapid, high-specificity, low-cost diagnostic techniques, since it can be presented, for example, as an immunochromatographic test.

SUMMARY DESCRIPTION OF THE INVENTION

The present invention relates to the use of a specific monoclonal antibody to diagnose infections caused by any of the HSV-1 and HSV-2 alphaherpesviruses.

Specifically, the monoclonal antibody developed as part of the invention proposed here, called 11B2C7, recognizes with high specificity the VP21 antigen of the capsid of HSV-1 and HSV-2, which is correlated with the presence of the HSV-1 and HSV-2 virus. This allows the detection, or diagnosis, of the presence of the virus in isolated samples from patients suspected of being infected by one of these viruses. The antibody of the invention is obtained in its pure state and free of any other contaminating biological material, so it can be easily used in various different formats leading to the detection and/or determination of infection by HSV-1 and HSV-2.

In a preferred aspect of the invention, the antibody of the invention can be used for assays for the detection and/or determination of infection caused by HSV-1.

In another preferred aspect, the antibody of the invention can be used for assays for the detection and/or determination of infection caused by HSV-2.

In another aspect of the invention, a method is provided for the prevention and treatment of infection caused by HSV-1 and/or HSV-2 in a given host, which comprises the administration of a composition comprising the monoclonal antibody of the invention, in doses sufficient to prevent and treat the disease. In the case of human use, the antibody can be humanized to minimize the possibility of an immune response against the host (patient) that uses it.

Furthermore, the invention makes it possible to provide the formulation of any pharmaceutical form of the monoclonal antibody of this invention and which are suitable for the diagnosis, treatment or prevention of infection caused by HSV-1 and/or HSV-2.

The antibody of the invention can also be implemented in different methods of diagnosis and detection of HSV-1 and/or HSV-2 viral antigens in biological samples, for example in tests such as: ELISA, Fluorescence microscopy (Immunofluorescence), Immunohistochemistry, Flow cytometry, Cell purification (Cell Sorter, by fluorescence, by association with magnetic spheres or any separation method that uses the antibody), Immunoprecipitation, Western blot and Chromatography. The samples can be in vitro cells infected with HSV-1 and/or HSV-2 or samples obtained from individuals suspected of infection by HSV-1 and HSV-2. In the case of samples from an individual, they may correspond to oral swabs, eye swabs, mucosa swabs, brain-spinal fluid, or any other type of sample that is considered appropriate.

The invention also provides the opportunity to develop a method of isolation and detection of HSV-1 and/or HSV-2 in biological samples and cell cultures that are brought into contact with the monoclonal antibody provided in this invention, coupled in any type of solid support, such as nitrocellulose, nylon membrane or other support.

In a preferred aspect, the antibody of the invention is useful in the development of rapid detection kits for HSV-1 and/or HSV-2 or similar alphaherpesviruses, which contain antigenic segments recognizable by the antibody of the invention disclosed herein.

In addition, the antibody of this invention provides the possibility of incorporating any type of chemically bound molecule or substrate, such as fluorophores, biotin, radio-isotopes, metals, enzymes and/or any chemical element coupled to the mentioned monoclonal antibody, as a method of detection, treatment, analysis and/or diagnosis in biological samples.

DESCRIPTION OF THE FIGURES

FIG. 1: Detection of HSV-1 and HSV-2 antigens by 11B2C7 antibody in Direct ELISA. This figure shows the specificity of the monoclonal antibody 11B2C7 of the invention in direct ELISA assays using as antigens, protein extracts of VERO cells (ATCC® CCL-81™ *Cercopithecus aethiops*, kidney epithelial cells) infected with HSV-1 (viral strain reference KOS) or HSV-2 (strain reference G). In this test, the following were included as negative control: uninfected and HSV-2 extract only incubated with secondary antibody ((−)1rio).

FIG. 2: Detection of HSV-1 and HSV-2 antigens by 11B2C7 antibody in sandwich ELISA. The reactivity in sandwich ELISA assay of the antibody of the invention was evaluated using antibody of the hybridoma clone 11B2C7 against protein extracts, both from VERO cells infected with HSV-1 (viral strain reference KOS) (HSV-1 KOS), and of VERO cells infected with HSV-2 (strain reference G) (HSV-2 G). Two negative controls (uninfected and (−)1rio)

were included. Negative control uninfected: capture and detection of 11B2C7 antibodies on an extract of uninfected cells, Negative control (−)1rio: detection antibody only tested on HSV-2 antibody extract without capture ((−)1rio). Additionally, the 11B2C7 antibody was tested against 500 ng of recombinant proteins VP21 of HSV-1 (VP21-1) and VP21 of HSV-2 (VP21-2), produced in *E. coli* and purified.

FIG. 4: Detection of HSV-1 and HSV-2 Antigens by Antibody 11B2C7 by Fluorescence Microscopy. Immunofluorescence assays with cell samples infected with HSV-1 and HSV-2 or non-infected, using the 11B2C7 antibody. VERO cells were infected with HSV-1 or HSV-2, fixed with acetone and incubated with the 11B2C7 antibody in a humid chamber. After saline washes, the sample was incubated with a secondary antibody against mouse IgG conjugated to the fluorophore FITC. Row 1: uninfected cells, Row 2: cells infected with HSV-1 (KOS), Row 3: cells infected with HSV-2 (G). The columns correspond to the different antibodies used to evaluate infection or non-specific reactivity. Column 1: Millipore® DFA® Commercial Kit from Light Diagnostics® catalog number 3291; Column 2: 11B2C7 antibody. The cells that appear white correspond to cells detected as infected with HSV-1 or HSV-2. As shown in the figure, the 11B2C7 antibody showed the ability to recognize cells infected with HSV-1 and HSV-2 similarly or better than the Millipore® DFA® commercial kit from Light Diagnostics®.

FIG. 5: Detection of HSV-1 and HSV-2 Antigens by 11B2C7 Antibody by Flow Cytometry. HeLa cell monolayers were infected with A. herpes simplex virus 1 (HSV-1 KOS) or B. herpes simplex virus 2 (HSV-2 G). The infected cells were released from the culture plate with trypsin and were washed with saline solution and then fixed with 2% paraformaldehyde in saline solution. The cells were then permeabilized with 0.5% saponin in saline and incubated with 11B2C7 antibody. Then, they were washed with saline solution and incubated with secondary antibody against mouse IgG conjugated to allophycocyanin fluorophore (APC). The cells were then washed once more with saline solution and resuspended in the same solution to proceed to measurement by flow cytometry. Negative controls correspond to 1. Uninfected cells to which 11B2C7 antibody was applied and then secondary antibody (uninfected) and 2. Uninfected cells to which only secondary antibody without 11B2C7 antibody was applied ((−)1rio). As a positive control to detect HSV-1 infection (KOS), the primary anti-gB antibody (Ac anti-gB, panel A) was used. As a positive control to detect HSV-2 (G) infection, the primary anti-gB antibody (Ac anti-gD, panel B) was used. The figure indicates the percentages of cells that present a fluorescence intensity associated with the detection of HSV antigen higher than that of uninfected cells treated with the 11B2C7 antibody.

DETAILED DESCRIPTION OF THE INVENTION

The present invention provides a monoclonal antibody that is capable of recognizing both HSV-1 and HSV-2, which specifically binds to the VP21 protein of the HSV-1 capsid, and; making this new antibody a useful alternative for the detection, diagnosis and specific treatment of infection caused by herpes simplex virus 1 and/or 2 (HSV).

The monoclonal antibody or fragments thereof that are part of this invention have been produced by immunizing mice using as antigen, the VP21 capsid protein encoded by the UL26 gene of the herpes simplex virus (HSV-1; herpes simplex virus type 1) whose sequence has been optimized to increase its expression in *E. coli* and which corresponds to the sequence SEQ ID No17. This monoclonal antibody was obtained from a cell line between several monoclonal hybridomas obtained against VP21 of HSV-1, and which we designate here as 11B2C7, of isotype IgG1, K, and which is capable of specifically recognizing HSV-1 and HSV-2.

Preferably, the monoclonal antibody of the invention is useful for recognizing with high specificity herpes simplex virus type 1 (HSV-1) and herpes simplex virus type 2 (HSV-2).

In summary, a monoclonal antibody is a type of homogeneous antibody that is characterized by specifically recognizing a single antigen and is produced by a single hybrid cell (hybridoma), which is the product of the fusion of a B lymphocyte clone and a tumor plasma cell.

The property of specifically binding and with high affinity to an antigen has promoted the development of monoclonal antibodies as a very useful tool for the detection of molecules that generate great scientific, clinical and industrial interest. Currently, monoclonal antibodies are widely used, both in basic and applied research, due to their specificity and reproducibility, which allows for a better foundation for research. However, it is in the area of biomedicine where monoclonal antibodies have had enormous practical applications, either for diagnosis and treatment of multiple infectious diseases, and as therapy for other pathologies. Although it is true that monoclonal antibodies are used in all types of detection and diagnostic techniques, it is in the design of kits for in vitro diagnosis that the best results have been obtained. For this, there are currently various rapid detection kits, such as the pregnancy test, which is based on the determination of chorionic gonadotropin (hCG) levels in the urine using anti-hCG antibody. Furthermore, monoclonal antibodies for therapeutic use have gained great relevance. Currently there are therapeutic treatments for different pathologies, through the use of commercial monoclonal antibodies such as: Alemtuzumab, Gemtuzumab ozogamicin, Rituximab, Trastumab, etc.

The monoclonal antibody of the invention can be used complete, as secreted by the hybridoma, or also as antigen-binding fragments. Antigen-binding fragments are fragments of the antibody capable of binding antigen, such as the fragments Fab or Fab'. In the present application, the applications of the antibody of the invention, while mentioning the use of the antibody, also include the use of binding fragments of the HSV-1 anti-VP21 monoclonal antibody.

Furthermore, in the case of the generation of compositions comprising the antibody of the invention, said compositions can comprise the murine antibody or the humanized or chimeric antibody of the invention. This is especially useful in compositions for human administration, as a way of minimizing the possibility that the immune system of the individual treated with the composition will generate a response against the antibody of the invention.

Thus, the invention aims at a monoclonal antibody or a fragment thereof that is specifically recognized by herpes simplex virus type 1 (HSV-1) and herpes simplex virus type 2 (HSV-2), where said antibody has a heavy chain variable region whose CDR1, CDR2 and CDR3 have amino acid sequences that have at least 95%, 96%, 97%, 98%, 99% or 100% identity with SEQ ID No:3, SEQ ID No:4 and SEQ ID No:5, respectively, and has a light chain variable region whose CDR1, CDR2 and CDR3, have sequences that have at least 95%, 96%, 97%, 98%, 99% or 100% identity with SEQ ID No:6, SEQ ID No:7 and SEQ ID No:8, respectively. More specifically said antibody has a variable region of the heavy chain with at least 95%, 96%, 97%, 98%, 99% or 100% identity with SEQ ID No:1 and has a variable region of the chain lightweight with at least 95% identity to SEQ ID No:2. Or alternatively, the antibody in its heavy chain variable region can be defined to be encoded in a nucleotide sequence that is at least 90%, 91%, 92%, 93%, 94%, 95%, 96%, 97%, 98%, 99% or 100% identity to SEQ ID No:9 and its light chain variable region is encoded in a nucleotide sequence that is at least 90%, 91%, 92%, 93%, 94%, 95%, 96%, 97%, 98%, 99% or 100% identity with SEQ ID No:10. Or said antibody has a heavy chain variable region whose CDR1, CDR2 and CDR3 are encoded in a nucleotide sequence that is at least 90%, 91%, 92%, 93%, 94%, 95%, 96%, 97%, 98%, 99% or 100% identity with SEQ ID No:11, SEQ ID No:12 and SEQ ID No:13, respectively, and has a variable region of the light chain whose CDR1, CDR2 and CDR3, are encoded in nucleotide sequences that have at least 90%, 91%, 92%, 93%, 94%, 95%, 96%, 97%, 98%, 99% or 100% identity with SEQ ID No:14, SEQ ID No:15 and SEQ ID No:16, respectively. The monoclonal antibody or a fragment thereof that specifically recognizes the herpes simplex virus can be a humanized or chimeric antibody.

For those skilled in the art, it will be apparent that nucleotide sequences may have greater variability, due to the degeneracy of the genetic code.

Additionally, the invention aims at a pharmaceutical composition for the treatment and/or prophylaxis of infection caused by HSV-1 and/or HSV-2 which comprises the monoclonal antibody 11B2C7 of the invention and a pharmaceutically acceptable carrier.

In another aspect, the invention aims at a method for detecting HSV-1 and/or HSV-2 viruses in a sample that comprises contacting the sample with the monoclonal antibody of the invention 11B2C7 or a fragment thereof and detecting the binding of the antibody with the antigen. The technique used to detect the binding of the antibody with the antigen can correspond to ELISA, immunofluorescence, immunohistochemistry, immunochromatography, flow cytometry, cell sorter, immunoprecipitation, Western blot, or any other available in the art. In one embodiment, the antibody of the invention or fragment thereof is conjugated with a marker that allows its detection. Where the label is selected from the group consisting of fluorophores, biotin, radioisotopes, metals, enzymes, or any other available in the art. In one embodiment, the antibody of the invention or a fragment thereof is immobilized on a solid support; such as nitrocellulose, cellulose, polyethylene, and nylon.

In yet another aspect, the invention aims at a method of treatment or prophylaxis of an infection by HSV-1 and/or HSV-2 viruses which comprises administering a pharmaceutical composition comprising the monoclonal antibody of the invention and a pharmaceutically acceptable carrier, such as excipients and formulation aids for different pharmaceutical forms. Where the pharmaceutical forms can be injectable solution, lyophilized to prepare injectable solutions or any other that exists in the art.

Where said composition is administered intramuscularly, intravenously, or other.

Examples are described below that allow the demonstration of the different applications of the monoclonal antibody of the invention.

Example 1: Obtaining an Anti-VP21 Antibody of HSV-1

As mentioned throughout this description, for the development of the antibody of the invention, the VP21 protein of HSV-1 was chosen as the antigen to be recognized. For this, the viral gene coding for this viral protein, from the capsid of HSV-1 to the UL26 gene of HSV-1, was obtained by chemical synthesis, using optimized codons to favor its subsequent expression in *E. coli* KRX strains, from where it was purified to be used as antigen in the corresponding immunization process is described below.

The expression of the recombinant HSV-1 VP21 protein to be used as antigen was initially analyzed by means of techniques with a wide technical domain such as electrophoresis in SDS-PAGE gels stained with Coomassie blue and Western blot transfers for subsequent recognition with a monoclonal antibody against the 6×-His domain present in antigenic recombinant proteins.

VP21 of purified HSV-1 was immediately concentrated with known methodologies of centricons and dialysis bags, obtaining quantities over the milligram per milliliter for the viral protein. In this way, it was possible to obtain VP21 from HSV-1 in a high degree of purity and in appropriate quantities to be used in the immunization process and production of specific monoclonal antibodies against this recombinant protein.

As a result of immunization with VP21 of HSV-1, encoded by the UL26 gene modified according to this invention, five lines of hybridomas producing monoclonal antibodies against VP21 of HSV-1 were obtained, including the line 11B2C7; the latter, which was chosen as the producer of the antibody of this invention, given its greater efficiency in the binding and detection of HSV-1 and HSV-2, as shown below.

The specificity of the antibody obtained by both lines of selected hybridomas was evaluated both by direct ELISA, sandwich ELISA and Western blot, using the recombinant protein used for the production of this antibody as a positive control. The isotype, as well as the type of light chain possessed by the antibody obtained in this invention is IgG1,K for the 11B2C7 line.

Example 2: Evaluation of the Monoclonal Antibody in Direct Type ELISA Assays with Antigen Extracted from Cultures Infected with Herpes Simplex Virus (Laboratory Reference Strains)

Figure 1:
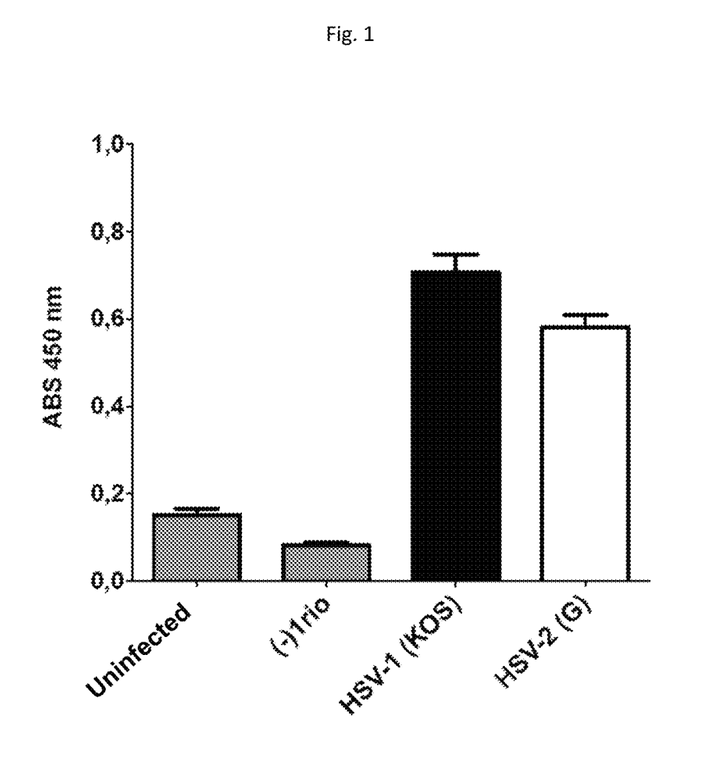

To evaluate the specificity of the antibody of the invention, a direct ELISA assay was performed on viral antigens extracted from epithelial cell cultures infected with herpes simplex virus 1 and 2 (HSV-1 and HSV-2). A culture of VERO cells (ATCC® CCL-81™ *Cercopithecus aethiops*, kidney epithelial cells) was used, which were infected with HSV-1 (viral strain reference KOS) or HSV-2 (viral strain reference G). Both groups of cells were infected with the virus; then it was harvested by centrifugation. The cell pellet obtained was used for total protein extraction using RIPA buffer (approximately 100-150 µL of buffer for every 10^7 cells). Then, the protein concentration was quantified by a BCA colorimetric assay. Once the total protein concentrations were known, the ELISA plates were activated with 50 µL of the protein extracts at a concentration of 10 µg/ml for two hours at room temperature. The plates were subsequently washed 3 times with 100 µL of PBS/0.05% Tween and then 5 times with PBS without Tween. Subsequently, all the wells of the plate were blocked with a 5% fetal bovine serum solution at room temperature. The previous wash scheme was then repeated on the plates and the primary antibody of the invention 11B2C7 was incubated for two hours at room temperature (5 µg per well). Then, the previous wash scheme was repeated on the plates and incubated with secondary mouse anti-IgG antibody conjugated to HRP (horseradish peroxidase). As a negative control, only secondary antibody was added to the extract of cells infected with HSV-2. Subsequently, it was developed with a PCB solution (35 mM citrate buffer, 67 mM phosphate, pH 5.0), TMB (3,3', 5,5'-tetramethyl-benzidine) 0.1 mg/ml and $H_2O_2$ 0.02% final concentration. The enzymatic reaction was allowed to proceed until prior to saturation. To stop the reaction, 10 µL of a 2N sulfuric acid solution was added and the absorbance was read in an ELISA reader at 450 nm on a Multiskan EX Thermo Labsystem equipment. The results are shown in FIG. 1.

In these tests it was observed that the antibody of the invention 11B2C7 reacted significantly against extracts of cells infected with reference strains of herpes simplex virus HSV-1 (KOS) and HSV-2 (G). The tested monoclonal antibody 11B2C7 reacted against HSV-1 and HSV-2.

Example 3: Evaluation of the Monoclonal Antibody 11B2C7 in Sandwich ELISA Assays with Antigen Extracted from Cultures Infected with Herpes Simplex Virus (Laboratory Reference Strains)

Figure 2:
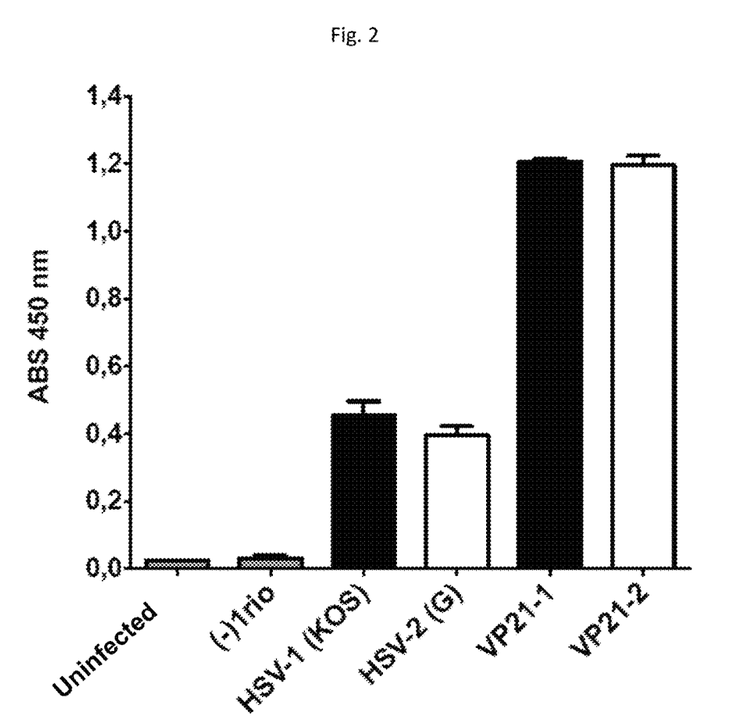

The reactivity of the antibody of the invention was evaluated against 1 ug of protein extract from VERO cells infected with HSV-1 (reference viral strain KOS) or with HSV-2 (reference viral strain G) and against recombinant proteins VP21 of HSV-1 and HSV-2, obtained in *E. coli* and purified. The ELISA plate was activated with 50 ul of the 11B2C7 antibody as capture antibody at a concentration of 12 ng/µL at room temperature. The capture antibody was then removed and all wells of the plate were blocked with a 5% fetal bovine serum solution at room temperature. Subsequently, the plate was washed 3 times with 100 µL of PBS/0.05% Tween and then 5 times with PBS without Tween. Then, 1 ug of the protein extract was applied and the plate was incubated at room temperature. Next, 50 ul of the detection antibody 11B2C7 conjugated to HRP (horseradish peroxidase) was added at 6 ng/µL. It was incubated for 30 min and washed before adding the developer solution. Subsequently, it was developed with a PCB solution (35 mM citrate buffer, 67 mM phosphate, pH 5.0), TMB (3,3', 5,5'-tetramethyl-benzidine) 0.1 mg/ml and $H_2O_2$ 0.02% final concentration. The enzymatic reaction was allowed to proceed until prior to saturation. To stop the reaction, 10 µL of a 2N sulfuric acid solution was added and the absorbance was read in an ELISA reader at 450 nm on a Multiskan EX Thermo Labsystem equipment. The results are shown in FIG. 2, where the ability of the monoclonal antibody of the invention (11B2C7) to recognize protein extracts infected with both HSV-1 and HSV-2, as well as a control that demonstrates its recognition of the VP21 protein from both viruses.

Figure 3:
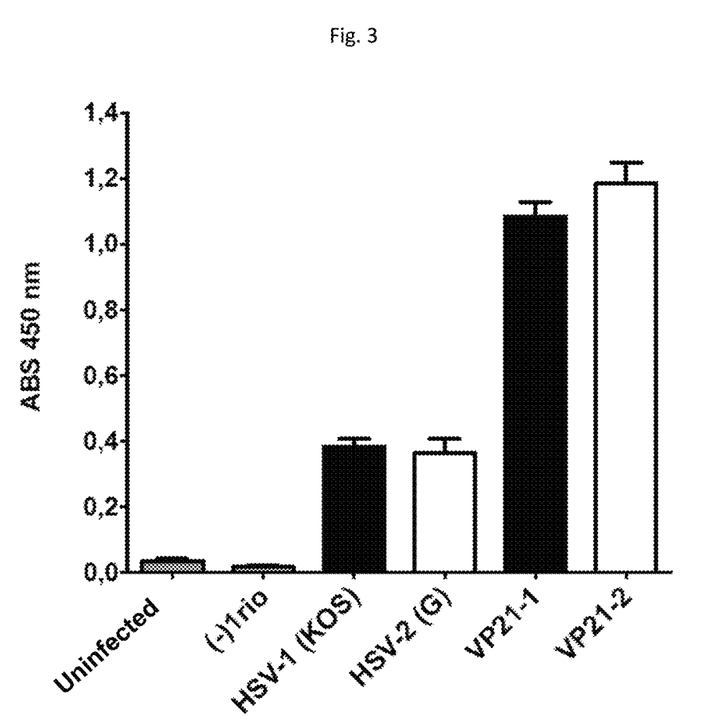
FIG. 3: Detection of antigens from clinical isolates of HSV-1 and HSV-2 by the 11B2C7 antibody in sandwich ELISA. The reactivity of the antibody of the invention in the sandwich ELISA assay was evaluated using antibody of the hybridoma clone 11B2C7 against protein extract of VERO cells inoculated with clinical isolates of HSV-1 and HSV-2 from which proteins (HSV-1 and HSV-2) were extracted. Two negative controls (uninfected and (−)1rio) were included. Negative control uninfected: 11B2C7 antibodies capture and detection on an extract of uninfected cells, Negative control (−) 1rio: only detection antibody evaluated on HSV-2 extract without capture antibody ((−) 1rio). Additionally, the 11B2C7 antibody was tested against 500 ng of recombinant proteins VP21 of HSV-1 (VP21-1) and VP21 of HSV-2 (VP21-2), produced in *E. coli* and purified.

Example 4: Evaluation of the Monoclonal Antibody 11B2C7 in Sandwich ELISA Assays with HSV Strains Obtained from Clinical Samples To evaluate the efficacy of the antibody of the invention in recognizing clinical isolates of HSV, we worked with strains of HSV obtained from clinical samples. For this, clinical isolates were obtained from patients with HSV-1 or HSV-2 infections, which were cultured (amplified) in VERO cells, permissive for the HSV-1 and HSV-2 viruses, from which proteins were extracted. The ELISA plate was activated with 50 ul of the 11B2C7 antibody as capture antibody at a concentration of 12 ng/µL at room temperature. The capture antibody was then removed and all wells of the plate were blocked with a 5% fetal bovine serum solution at room temperature. Subsequently, the plate was washed 3 times with 100 µL of PBS/0.05% Tween and then 5 times with PBS without Tween. Then, 1 ug of the protein extract was applied and the plate was incubated at room temperature. Next, 50 ul of detection antibody 11B2C7 conjugated to HRP (horseradish peroxidase) was added at 6 ng/µL. It was incubated for 30 min and washed before adding the developer solution. Subsequently, it was developed with a PCB solution (35 mM citrate buffer, 67 mM phosphate, pH 5.0), TMB (3,3', 5,5'-tetramethyl-benzidine) 0.1 mg/ml and $H_2O_2$ 0.02% final concentration. The enzymatic reaction was allowed to proceed until prior to saturation. To stop the reaction, 10 µL of a 2N sulfuric acid solution was added and the absorbance was read in an ELISA reader at 450 nm on a Multiskan EX Thermo Labsystem equipment. The results are shown in FIG. 3, where the ability of the monoclonal antibody of the invention (11B2C7) to recognize protein extracts infected with both clinical isolates of HSV-1 and HSV-2 is evidenced, as well as a control that demonstrates its recognition of the VP21 protein of both viruses.

Example 5: Immunofluorescence Assays with Samples of Cells Infected with HSV, Using the Antibody Developed Against VP21 of HSV-1

Figure 4:
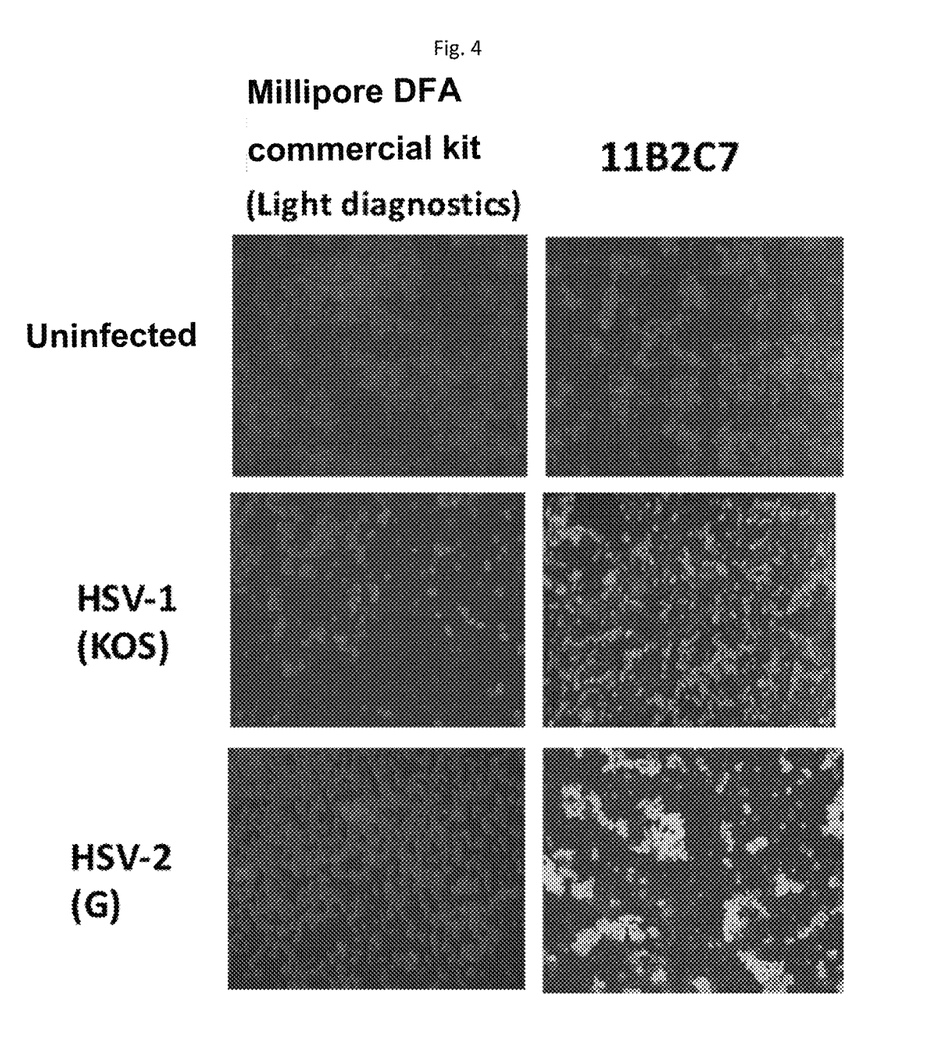

Immunofluorescence assays were performed with the antibody of the invention 11B2C7 and compared with a commercial kit. VERO cells were infected with HSV-1 or HSV-2 and then released from the plates with trypsin, washed with saline, and placed on a slide until the sample was dry. Next, 50 ul of acetone was applied to fix the cells and after washing with saline solution, the antibody 11B2C7 (12 ng/µL) was applied in a humid chamber. After saline washes, the sample was incubated with a secondary antibody against mouse IgG conjugated to the fluorophore FITC. In FIG. 4, the rows correspond to treatment conditions. Row 1: uninfected cells, Row 2: cells infected with HSV-1 (KOS), Row 3: cells infected with HSV-2 (G). The columns correspond to the different antibodies used to evaluate infection or non-specific reactivity. Column 1: Millipore® DFA® Commercial Kit from Light Diagnostics® catalog number 3291; Column 2: 11B2C7 antibody. The cells that appear white (clear) correspond to cells detected as infected (positive infection) with HSV-1 or HSV-2. As shown in FIG. 4, the 11B2C7 antibody showed the ability to recognize HSV-1 and HSV-2 infected cells similarly or better than the Millipore® DFA® commercial kit from Light Diagnostics®. With this, it is once again confirmed that the antibody of the invention 11B2C7 is capable of recognizing cells infected with HSV-1 and/or HSV-2, also in immunofluorescence assays.

Figure 5:
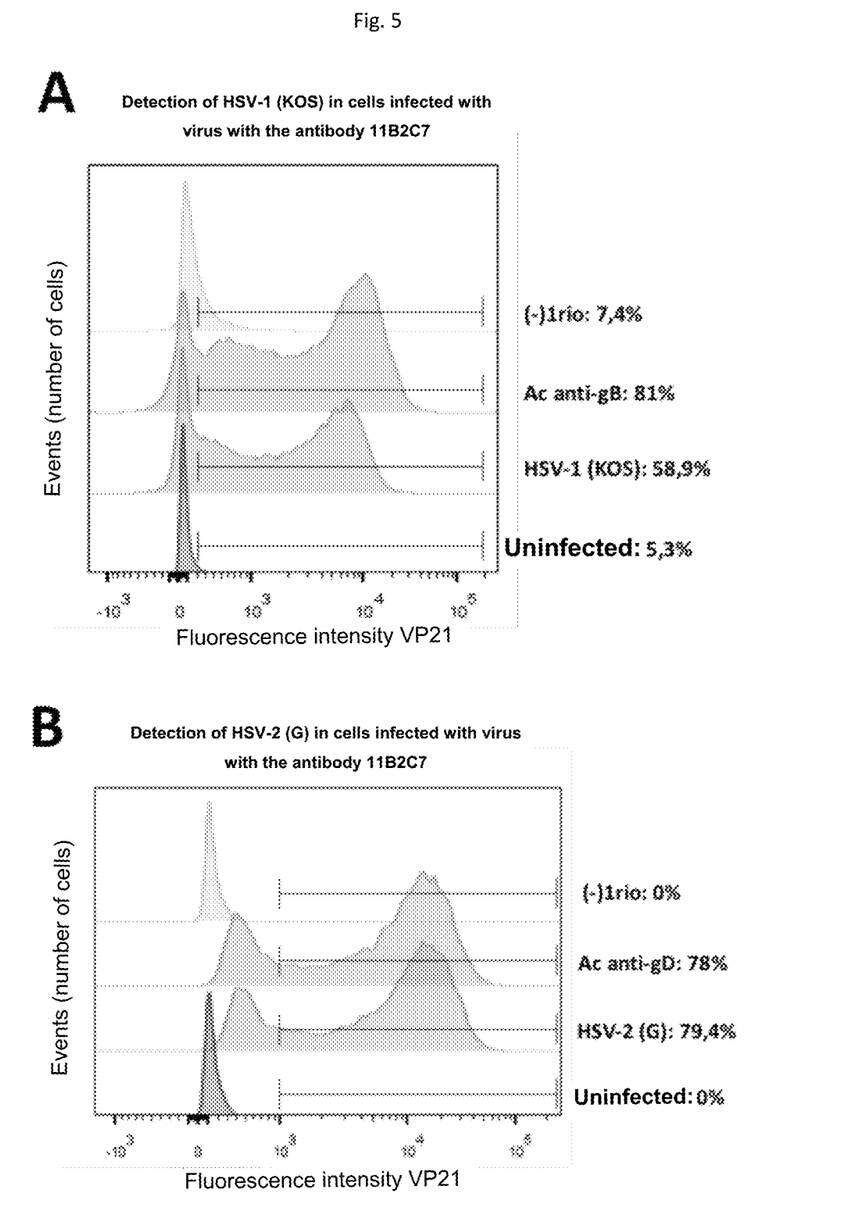

Example 6: Cytometry of Cells Infected with HSV-1 Virus and Intracellularly Labeled with the 11B2C7 Antibody of the Invention HeLa cell monolayers (ATCC #CCL-2, *Homo sapiens*, cervix) were infected with herpes simplex virus 1 (strain KOS) or herpes simplex virus 2 (strain G). Post-infection, cells were released from the plate with trypsin and separated by centrifugation. The resulting cell pellet was resuspended in a saline solution with 2% paraformaldehyde and incubated for virus inactivation. Subsequently, the cells were washed with saline solution, centrifuged and resuspended in a 0.5% saline/Saponin solution in order to permeabilize the already fixed cells. After 15 minutes of incubation, the cells were centrifuged, and resuspended in a saline/0.5% Saponin solution plus the primary antibody 11B2C7, adding 2 µg total of antibody per 10"6 cells in a volume of 100 µL. After incubation at 4° C., cells were washed with saline. Subsequently, cells were resuspended in a solution containing a secondary antibody against mouse IgG conjugated to allophycocyanin (APC) and the sample was observed on a FACS-Canto II, BD flow cytometer. In order to corroborate the specificity of the antibody, the above protocol was performed with 11B2C7 antibody and secondary antibody on uninfected cells. The graph of FIG. 5 expresses the percentage of fluorescence intensity associated with the detection of antigen versus the same antibody against uninfected cells. The antibody of the invention showed specificity for infected cells and allowed the discrimination of infected cells from non-infected cells.

Example 7: Sequencing of the Antibody of the Invention

The antibody of the invention 11B2C7, produced by the hybridoma 11B2C7, was sequenced. The protein sequences of the heavy chain are shown in SEQ ID No1, and that of the light chain in SEQ ID No2, and the amino acid sequences for the CDRs are identified in:
SEQ ID No3 for CDR1, Heavy chain;
SEQ ID No4 for CDR2, Heavy chain;
SEQ ID No5 for CDR3, Heavy chain;
SEQ ID No6 for CDR1, Light chain;
SEQ ID No7 for CDR2, Light chain;
SEQ ID No8 for CDR3, Light chain.

While the coding nucleotide sequences for the variable regions of each sequence are shown in SEQ ID No9 for the heavy chain and in SEQ ID No10 for the light chain, and the nucleotide sequences for the CDRs are identified in:
SEQ ID No11 for CDR1, Heavy chain;
SEQ ID No12 for CDR2, Heavy chain;
SEQ ID No13 for CDR3, Heavy chain;
SEQ ID No14 for CDR1, Light chain;
SEQ ID No15 for CDR2, Light chain;
SEQ ID No16 for CDR3, Light chain.

The invention claimed is:

1. A monoclonal antibody or an antigen-binding fragment thereof that specifically recognizes herpes simplex virus type 1 (HSV-1) and herpes simplex virus type 2 (HSV-2), wherein said antibody or the antigen-binding fragment thereof has a variable region of a heavy chain in which CDR1, CDR2, and CDR3 have amino acid sequences defined in SEQ ID No:3, SEQ ID No:4, and SEQ ID No: 5, respectively, and at the same time has a variable region of a light chain in which CDR1, CDR2, and CDR3 have amino acid sequences defined in SEQ ID No:6, SEQ ID No:7, and SEQ ID No:8, respectively.

2. The monoclonal antibody or the antigen-binding fragment thereof according to claim 1, wherein said monoclonal antibody or the antigen-binding fragment thereof has the variable region of the heavy chain in which the CDR1, the CDR2, and the CDR3 are encoded by sequences that have at least 90% identity with SEQ ID No:11, SEQ ID No:12, and SEQ ID No: 13, respectively, and has the variable region of the light chain in which the CDR1, the CDR2, and the CDR3 are encoded by sequences that have at least 90% identity with SEQ ID No:14, SEQ ID No:15, and SEQ ID No:16, respectively.

3. The monoclonal antibody or the antigen-binding fragment thereof according to claim 1, wherein the monoclonal antibody or the antigen-binding fragment thereof is specific against protein VP21 of a capsid of the HSV-1 and the HSV-2.

4. The monoclonal antibody or the antigen-binding fragment thereof according to claim 1, wherein the antibody is a humanized or a chimeric antibody.

5. A pharmaceutical composition for treatment and/or prophylaxis of infection caused by HSV-1 and/or HSV-2, comprising:

the monoclonal antibody or the antigen-binding fragment thereof of claim 1; and
a pharmaceutically acceptable carrier.

6. A method for detection of HSV-1 and/or HSV-2 virus in a sample, comprising:
contacting the sample with the monoclonal antibody or the antigen-binding fragment thereof of claim 1; and
detecting a binding of the monoclonal antibody or the antigen-binding fragment thereof to the HSV-1 or the HSV-2 or both, as an antigen in the sample.

7. The method according to claim 6, wherein the method used to detect the binding of the monoclonal antibody or the antigen-binding fragment thereof to the antigen is at least one technique selected from the group consisting of ELISA, immunofluorescence, immunohistochemistry, immunochromatography, flow cytometry, cell sorting, immunoprecipitation, and western blotting.

8. A method for detection of HSV-1 and/or HSV-2 virus in a sample, comprising:
contacting the sample with the monoclonal antibody or the antigen-binding fragment thereof according to claim 1; and
detecting a binding of the monoclonal antibody or the antigen binding fragment thereof to the HSV-1 or the HSV-2 or both, as an antigen in the sample, wherein the monoclonal antibody or the antigen-binding fragment thereof is conjugated with a marker that allows detection of a presence of the monoclonal antibody or the antigen-binding fragment thereof.

9. The method according to claim 8, wherein the marker is a label selected from the group consisting of fluorophores, biotin, radioisotopes, metals, and enzymes.

10. The method according to claim 8, wherein the monoclonal antibody or the antigen binding fragment thereof is immobilized on a solid support.

11. The method according to claim 10, wherein the solid support is a support selected from the group consisting of nitrocellulose, cellulose, polyethylene, nylon, and other immunochromatography-compatible solid supports.

12. The method according to claim 6, wherein the sample is a sample selected from the group consisting of a swab that has been contacted with mouth, skin, eye, or mucosa, samples of plasma or brain-spinal fluid, and any other samples in which presence of the HSV-1, or the HSV-2 virus, or both is suspected.

* * * * *

SEQUENCE LISTING

```
<160> NUMBER OF SEQ ID NOS: 17

<210> SEQ ID NO 1
<211> LENGTH: 135
<212> TYPE: PRT
<213> ORGANISM: MURINE

<400> SEQUENCE: 1

Met Gly Trp Ser Cys Ile Ile Phe Phe Leu Val Ala Thr Ala Thr Gly
1               5                   10                  15

Val His Ser Gln Val Gln Leu Gln Gln Ser Gly Pro Glu Leu Val Arg
            20                  25                  30

Pro Gly Glu Ser Val Lys Ile Ser Cys Lys Gly Ser Gly Tyr Thr Phe
        35                  40                  45

Thr Asp Tyr Thr Met His Trp Val Lys Gln Ser His Ala Lys Ser Leu
    50                  55                  60

Glu Trp Ile Gly Val Ile Ser Ile Tyr Tyr Asp Asn Thr Asn Tyr Asn
65                  70                  75                  80

Gln Lys Phe Lys Gly Lys Ala Thr Met Thr Val Asp Lys Ser Ser Ser
                85                  90                  95

Thr Ala Tyr Met Glu Leu Ala Arg Leu Thr Ser Glu Asp Ser Ala Ile
            100                 105                 110

Tyr Tyr Cys Ala Arg Gly Gly Thr Gly Phe Ala Tyr Trp Gly Gln Gly
        115                 120                 125

Thr Leu Val Thr Val Ser Ala
    130                 135

<210> SEQ ID NO 2
<211> LENGTH: 131
<212> TYPE: PRT
```

<213> ORGANISM: MURINE

<400> SEQUENCE: 2

Met Glu Thr Asp Thr Ile Leu Leu Trp Val Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Ser Tyr Met Asn Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln Gln Ser Asn Glu Asp Pro Trp Thr Phe Gly Gly Gly Thr Lys Leu
        115                 120                 125

Glu Ile Lys
    130

<210> SEQ ID NO 3
<211> LENGTH: 5
<212> TYPE: PRT
<213> ORGANISM: MURINE

<400> SEQUENCE: 3

Asp Tyr Thr Met His
1               5

<210> SEQ ID NO 4
<211> LENGTH: 17
<212> TYPE: PRT
<213> ORGANISM: MURINE

<400> SEQUENCE: 4

Val Ile Ser Ile Tyr Tyr Asp Asn Thr Asn Tyr Asn Gln Lys Phe Lys
1               5                   10                  15
Gly

<210> SEQ ID NO 5
<211> LENGTH: 7
<212> TYPE: PRT
<213> ORGANISM: MURINE

<400> SEQUENCE: 5

Gly Gly Thr Gly Phe Ala Tyr
1               5

<210> SEQ ID NO 6
<211> LENGTH: 15
<212> TYPE: PRT
<213> ORGANISM: MURINE

<400> SEQUENCE: 6

Lys Ala Ser Gln Ser Val Asp Tyr Asp Gly Asp Ser Tyr Met Asn
1               5                   10                  15

<210> SEQ ID NO 7

```
<211> LENGTH: 7
<212> TYPE: PRT
<213> ORGANISM: MURINE

<400> SEQUENCE: 7

Ala Ala Ser Asn Leu Glu Ser
1               5

<210> SEQ ID NO 8
<211> LENGTH: 9
<212> TYPE: PRT
<213> ORGANISM: MURINE

<400> SEQUENCE: 8

Gln Gln Ser Asn Glu Asp Pro Trp Thr
1               5

<210> SEQ ID NO 9
<211> LENGTH: 405
<212> TYPE: DNA
<213> ORGANISM: MURINE

<400> SEQUENCE: 9
atgggttgga gctgtatcat cttctttctg gtagcaacag ctacaggtgt gcactcccag      60
gtccagctgc agcagtctgg gcctgagctg gtgaggcctg gggaatcagt gaagatttcc    120
tgcaagggtt ccggctacac attcactgat tatactatgc actgggtgaa gcagagtcat    180
gcaaagagtc tagagtggat tggagttatt agtatttact atgataatac aaactacaac    240
cagaagttta aggcaaggc cacaatgact gtagacaaat cctccagcac agcctatatg    300
gaacttgcca gattgacatc tgaggattct gccatctatt actgtgcaag aggggggacg    360
gggtttgctt actggggcca aggactctg gtcactgtct ctgca                      405

<210> SEQ ID NO 10
<211> LENGTH: 393
<212> TYPE: DNA
<213> ORGANISM: MURINE

<400> SEQUENCE: 10
atggagacag acacaatcct gctatgggtg ctgctgctct gggttccagg ctccactggt     60
gacattgtgc tgacccaatc tccagcttct ttggctgtgt ctctagggca gagggccacc   120
atctcctgca aggccagcca agtgttgat tatgatggtg atagttatat gaactggtac    180
caacagaaac caggacagcc acccaaactc ctcatctatg ctgcatccaa tctagaatct   240
gggatcccag ccaggtttag tggcagtggg tctgggacag acttcaccct caacatccat   300
cctgtggagg aggaggatgc tgcaacctat tactgtcagc aaagtaatga ggatccgtgg   360
acgttcggtg gaggcaccaa gctggaaatc aaa                                  393

<210> SEQ ID NO 11
<211> LENGTH: 14
<212> TYPE: DNA
<213> ORGANISM: MURINE

<400> SEQUENCE: 11
gattatacta tgca                                                        14

<210> SEQ ID NO 12
<211> LENGTH: 51
<212> TYPE: DNA
<213> ORGANISM: MURINE
```

<400> SEQUENCE: 12
gttattagta tttactatga taatacaaac tacaaccaga agtttaaggg c         51

<210> SEQ ID NO 13
<211> LENGTH: 21
<212> TYPE: DNA
<213> ORGANISM: MURINE

<400> SEQUENCE: 13 gggggacgg ggtttgctta c                                           21

<210> SEQ ID NO 14
<211> LENGTH: 45
<212> TYPE: DNA
<213> ORGANISM: MURINE

<400> SEQUENCE: 14
aaggccagcc aaagtgttga ttatgatggt gatagttata tgaac                45

<210> SEQ ID NO 15
<211> LENGTH: 21
<212> TYPE: DNA
<213> ORGANISM: MURINE

<400> SEQUENCE: 15
gctgcatcca atctagaatc t                                          21

<210> SEQ ID NO 16
<211> LENGTH: 27
<212> TYPE: DNA
<213> ORGANISM: MURINE

<400> SEQUENCE: 16
cagcaaagta atgaggatcc gtggacg                                    27

<210> SEQ ID NO 17
<211> LENGTH: 1908
<212> TYPE: DNA
<213> ORGANISM: Human herpesvirus 1

<400> SEQUENCE: 17
atggctgcag atgcaccagg tgaccgtatg gaagaaccgc tgccagatcg tgcggttccg      60
atctacgttg caggtttcct ggcactgtac gatagcggtg actccggtga gctggctctg     120
gacccagaca ccgttcgtgc agcactgcca ccagacaacc cactgccgat caacgtagac     180
catcgtgcag ttgtgaggt tggtcgtgta ctggcagttg tggacgatcc acgtggtccg     240
ttcttcgtgg gtctgatcgc gtgcgttcaa ctggaacgtt ttctggaaac cgcagcatct     300
gcagctatct tcgaacgccg tggtccacca ctgtcccgtg aagagcgcct gctgtatctg     360
attaccaact atctgccatc cgtgtccctg gctaccaaac gtctgggtgg tgaagcgcat     420
ccggatcgta tctctgttcg cgcacgttgcg ctgtgtgcta ttggtcgtcg tctgggtact     480
atcgtgacct acgacaccgg tctggacgca gctattgcac cgttccgtca cctgagccca     540
gctagccgtg aaggtgctcg tcgtctggca gctgaggcca gctggccct gtctggtcgc     600 acctgggctc cgggtgtgga agcactgacc catacccctgc tgtccaccgc agtgaacaac     660
atgatgctgc gtgatcgctg gtccctggta gctgagcgtc gtcgtcaggc aggtatcgct     720
ggtcacacct acctgcaagc atctgagaag ttcaagatgt ggggcgcgga gccggtaagc     780

```
gctccggcac gtggttacaa gaatggtgct ccagagtcca ctgacattcc accaggttcc    840
attgcagctg ctccacaggg cgatcgttgt ccgattgtgc gtcagcgtgg tgtagctctg    900
tctccggtac tgccaccaat gaatccagtt ccgacctctg gcactccagc accggctcca    960
ccgggtgacg gtagctatct gtggattcca gctagccact acaaccaact ggtagcaggc   1020
catgcagcac cgcagccaca accgcactct gcgttcggct ttccggctgc cgcaggctcc   1080
gtagcttatg gcccacatgg tgcaggtctg tcccagcact atccaccgca cgtggcacac   1140
cagtatccgg gtgttctgtt ctccggtccg tctccgctgg aagcgcagat cgctgcactg   1200
gttggtgcga tcgctgccga ccgccaagct ggaggtcagc cagcagctgg tgatccgggt   1260
gtgcgtggta gcggtaaacg tcgtcgttac gaagcaggtc cgagcgaaag ctattgtgat   1320
caggacgagc cagacgctga ttacccatac tatccaggcg aagcacgtgg tgcaccacgt   1380
ggtgtggact ctcgtcgcgc tgcacgtcac tctccaggca ccaacgaaac catcactgcc   1440
ctgatgggtg ctgtgacctc tctgcaacag gaactggcgc acatgcgtgc ccgtacctcc   1500
gcaccatacg gtatgtacac tccggtggcg cactaccgtc cgcaggtagg cgaaccggaa   1560
ccgaccacta cccacccagc tctgtgtcca ccagaagctg tgtatcgtcc gccaccacat   1620
tctgctccgt atggtccacc acaaggtcca gcatctcacg caccaactcc accatacgct   1680
ccggctgcct gtccgccagg tccgccacca ccaccgtgtc catctaccca aactcgtgca   1740
ccactgccga ccgaaccggc attcccacca gctgcaactg gttctcagcc agaagcatcc   1800
aacgcagaag ctggtgcgct ggttaacgct tcctctgccg cacatgtgga cgtggacacc   1860
gctcgtgcag cggatctgtt tgtgagccag atgatgggtg cacgctaa                1908
```